United States Patent
Hudson et al.

(10) Patent No.: US 9,102,573 B2
(45) Date of Patent: Aug. 11, 2015

(54) ENCAPSULATED PARTICLE

(71) Applicant: BASF SE, Ludwigshafen (DE)

(72) Inventors: Alice Hudson, Jupiter, FL (US); Lillian Senior, Port St. Lucie, FL (US); Bernard Sencherey, Lake Jackson, TX (US); Victor Granquist, Jupiter, FL (US)

(73) Assignee: BASF SE, Ludwigshafen (DE)

( * ) Notice: Subject to any disclaimer, the term of this patent is extended or adjusted under 35 U.S.C. 154(b) by 77 days.

(21) Appl. No.: 13/896,651

(22) Filed: May 17, 2013

(65) Prior Publication Data

US 2013/0305796 A1  Nov. 21, 2013

Related U.S. Application Data

(60) Provisional application No. 61/648,697, filed on May 18, 2012.

(51) Int. Cl.

| C05B 17/00 | (2006.01) |
|---|---|
| C05C 9/00 | (2006.01) |
| C05C 3/00 | (2006.01) |
| C05D 1/00 | (2006.01) |
| B01J 13/14 | (2006.01) |
| A01N 25/28 | (2006.01) |
| C08G 18/50 | (2006.01) |
| C09D 175/04 | (2006.01) |
| C08G 18/48 | (2006.01) |
| C05G 3/00 | (2006.01) |

(52) U.S. Cl.
CPC ............... *C05B 17/00* (2013.01); *A01N 25/28* (2013.01); *B01J 13/14* (2013.01); *C05C 3/00* (2013.01); *C05C 9/00* (2013.01); *C05G 3/0029* (2013.01); *C05G 3/0035* (2013.01); *C08G 18/482* (2013.01); *C08G 18/5033* (2013.01); *C09D 175/04* (2013.01)

(58) Field of Classification Search
CPC ............ C05B 17/00; C05C 9/00; C05C 3/00; C05G 3/0035; C05G 3/0029; B01J 13/14; A01N 25/28; C08G 18/5033; C08G 18/482; C09D 175/04

See application file for complete search history.

(56) References Cited

U.S. PATENT DOCUMENTS

| 3,264,089 A | 8/1966 | Hansen |
|---|---|---|
| 4,588,803 A | 5/1986 | Christman |
| 4,711,659 A | 12/1987 | Moore |
| 4,804,403 A | 2/1989 | Moore |
| 5,219,465 A | 6/1993 | Goertz et al. |
| 5,300,135 A | 4/1994 | Hudson |
| 5,411,856 A | 5/1995 | Riecke et al. |
| 5,423,897 A | 6/1995 | Hudson et al. |
| 5,429,654 A | 7/1995 | Swarup |
| 5,466,274 A | 11/1995 | Hudson et al. |
| 5,478,375 A | 12/1995 | Hudson |
| 5,538,531 A | 7/1996 | Hudson et al. |
| 5,599,374 A | 2/1997 | Detrick |
| 5,698,002 A | 12/1997 | Hudson |
| 5,803,946 A | 9/1998 | Petcavich et al. |
| 5,984,994 A | 11/1999 | Hudson |
| 5,993,505 A | 11/1999 | Tijsma et al. |
| 6,001,147 A | 12/1999 | Markusch et al. |
| 6,039,781 A | 3/2000 | Goertz et al. |
| 6,165,550 A | 12/2000 | Markusch et al. |
| 6,322,606 B1 | 11/2001 | Komoriya et al. |
| 6,358,296 B1 | 3/2002 | Markusch et al. |
| 6,364,925 B1 | 4/2002 | Markusch et al. |
| 6,617,412 B2 | 9/2003 | Markusch et al. |
| 6,663,686 B1 | 12/2003 | Geiger et al. |
| 7,022,113 B2 | 4/2006 | Lockwood et al. |
| 7,267,707 B2 | 9/2007 | Rosenthal et al. |
| 7,416,785 B2 | 8/2008 | Mente |
| 7,452,399 B2 | 11/2008 | Whittington |
| 7,553,306 B1 | 6/2009 | Hunt et al. |
| 7,615,093 B2 | 11/2009 | Pildysh |
| 7,771,505 B2 | 8/2010 | Ogle et al. |
| 8,034,037 B2 | 10/2011 | Adams et al. |
| 8,303,680 B2 | 11/2012 | Mente |
| 2004/0260230 A1 | 12/2004 | Randolph |

(Continued)

FOREIGN PATENT DOCUMENTS

| EP | 0600351 A1 | 6/1994 |
|---|---|---|
| EP | 0 867 422 A2 | 9/1998 |

(Continued)

OTHER PUBLICATIONS

International Search Report for Application No. PCT/US2013/041571 dated Apr. 11, 2013, 12 pages.

(Continued)

*Primary Examiner* — Jennifer A Smith

(74) *Attorney, Agent, or Firm* — Howard & Howard Attorneys PLLC

(57) ABSTRACT

An encapsulated particle includes a core particle and a polyurethane disposed about the core particle. The polyurethane includes the reaction product of an aromatic isocyanate component and a polyol component. The polyol component includes a polyol derived from an aromatic amine-based initiator and an aliphatic polyether polyol. The polyol derived from the aromatic amine-based initiator has a nominal functionality of 4. The aliphatic polyether polyol has a nominal functionality of from 2 to 4. The weight ratio of the polyol derived from the aromatic amine-based initiator and the aliphatic polyether polyol is from about 1:2 to 2:1. A method of forming the encapsulated particle is also provided.

20 Claims, No Drawings

(56) References Cited

U.S. PATENT DOCUMENTS

| | | |
|---|---|---|
| 2005/0066697 A1 | 3/2005 | Cline et al. |
| 2005/0070858 A1 | 3/2005 | Lockwood et al. |
| 2005/0154359 A1 | 7/2005 | Charlez |
| 2005/0192548 A1 | 9/2005 | Dolliver et al. |
| 2005/0266245 A1 | 12/2005 | Mente |
| 2006/0032282 A1 | 2/2006 | Wynnyk et al. |
| 2006/0222735 A1 | 10/2006 | Rosenthal et al. |
| 2007/0100324 A1 | 5/2007 | Tempel et al. |
| 2007/0191538 A1 | 8/2007 | Apichatachutapan et al. |
| 2008/0125729 A1 | 5/2008 | Gradl |
| 2009/0012484 A1 | 1/2009 | Nielsen et al. |
| 2009/0221990 A1 | 9/2009 | Jaeb et al. |
| 2009/0240218 A1 | 9/2009 | Braga et al. |
| 2009/0264840 A1 | 10/2009 | Virginio |
| 2009/0292263 A1 | 11/2009 | Hudspeth et al. |
| 2009/0306630 A1 | 12/2009 | Locke et al. |
| 2009/0312728 A1 | 12/2009 | Randolph et al. |
| 2009/0326416 A1 | 12/2009 | McNulty et al. |
| 2009/0326488 A1 | 12/2009 | Budig et al. |
| 2010/0010477 A1 | 1/2010 | Augustine et al. |
| 2010/0011825 A1 | 1/2010 | Ogle et al. |
| 2010/0036333 A1 | 2/2010 | Schenk, III et al. |
| 2010/0063463 A1 | 3/2010 | Wiesner |
| 2010/0069858 A1 | 3/2010 | Olson |
| 2010/0145289 A1 | 6/2010 | Lina et al. |
| 2010/0160853 A1 | 6/2010 | Smith et al. |
| 2010/0168688 A1 | 7/2010 | Santora et al. |
| 2010/0179493 A1 | 7/2010 | Heagle et al. |
| 2010/0185165 A1 | 7/2010 | Middleton et al. |
| 2010/0204663 A1 | 8/2010 | Wudyka |
| 2010/0211030 A1 | 8/2010 | Turner et al. |
| 2010/0262091 A1 | 10/2010 | Larsson |
| 2010/0262096 A1 | 10/2010 | Hall |
| 2010/0268176 A1 | 10/2010 | Johnson et al. |
| 2010/0280422 A1 | 11/2010 | Hartwell |
| 2010/0286635 A1 | 11/2010 | Watson, Jr. |
| 2010/0286638 A1 | 11/2010 | Malhi |
| 2010/0298790 A1 | 11/2010 | Guidi et al. |
| 2010/0305523 A1 | 12/2010 | Vess |
| 2010/0326152 A1 | 12/2010 | Mente |
| 2011/0015590 A1 | 1/2011 | Svedman et al. |
| 2011/0022013 A1 | 1/2011 | Boynton et al. |
| 2011/0028921 A1 | 2/2011 | Hartwell et al. |
| 2011/0077605 A1 | 3/2011 | Karpowicz et al. |
| 2011/0105872 A1 | 5/2011 | Chickering, III et al. |
| 2011/0106027 A1 | 5/2011 | Vess et al. |
| 2011/0106030 A1 | 5/2011 | Scholz |
| 2011/0152799 A1 | 6/2011 | Kevin et al. |
| 2011/0196321 A1 | 8/2011 | Wudyka |
| 2011/0224631 A1 | 9/2011 | Simmons et al. |
| 2011/0270202 A1 | 11/2011 | Boehringer et al. |
| 2011/0276016 A1 | 11/2011 | Tsai |
| 2011/0288510 A1 | 11/2011 | Locke et al. |
| 2011/0295220 A1 | 12/2011 | Heaton et al. |

FOREIGN PATENT DOCUMENTS

| | | |
|---|---|---|
| WO | WO 2006/105239 A2 | 10/2006 |
| WO | WO 2013/173739 A2 | 11/2013 |
| WO | WO 2013/173748 A1 | 11/2013 |

OTHER PUBLICATIONS

Database CA [Online] Chemical Abstracts Service, Columbus, Ohio, US; XP000406959, Database accession No. XP000406959, ISSN: 0009-2258, Dec. 2, 1991, 1 page.

International Search Report for Application No. PCT/US2013/041640 dated Oct. 8, 2013, 4 pages.

International Search Report for Application No. PCT/US2013/041630 dated Apr. 3, 2014, 3 pages.

ENCAPSULATED PARTICLE

CROSS-REFERENCE TO RELATED APPLICATIONS

This application claims priority to U.S. Provisional Patent Application No. 61/648,697, filed on May 18, 2012, which is hereby incorporated by reference in its entirety.

This application is related to the following U.S. Non-Provisional patent applications assigned to the same assignee, each of which is incorporated herein by reference in its entirety: U.S. patent application Ser. No. 13/896,745, filed on May 17, 2013, entitled "A DUST SUPPRESSING AGGREGATE", with Raymond Neff, Alexander Gershanovich and Donald C. Mente as inventors; and U.S. patent application Ser. No. 13/896,975, filed on May 17, 2013, entitled "AN ENCAPSULATED PARTICLE", with Raymond Neff, Alexander Gershanovich and Donald C. Mente as inventors.

This application also incorporates by reference in its entirety and is related to U.S. Patent Provisional Application No. 61/648,766, filed on May 18, 2012.

FIELD OF THE INVENTION

The present invention generally relates to an encapsulated particle. More specifically, the invention relates to an encapsulated particle including a core particle and a polyurethane disposed about the core particle.

BACKGROUND OF THE INVENTION

Encapsulated particles, such as controlled-release fertilizers, are known in the agricultural art. These encapsulated particles typically include one or more polyurethanes disposed about a core particle. The thickness and integrity of the polyurethane limits the dissolution rate of the core particle into the soil. Unfortunately, many of the conventional encapsulated particles are brittle and may be damaged during normal handling, resulting in unpredictable and rapid dissolution of the core particle into the soil. These accelerated dissolution rates lead to waste and phytotoxicity. Accordingly, there remains an opportunity to develop an improved encapsulated particle.

SUMMARY OF THE INVENTION AND ADVANTAGES

An encapsulated particle includes a core particle and a polyurethane disposed about the core particle. The polyurethane includes the reaction product of an aromatic isocyanate component having a nominal functionality of at least 2 and a polyol component. The aromatic isocyanate component is utilized in an amount of from about 20 to 60 wt. % based on total weight of the aromatic isocyanate component and the polyol component. The polyol component is utilized in an amount of from about 40 to 80 wt. % based on the total weight of the aromatic isocyanate component and the polyol component. The polyol component includes an polyol derived from an aromatic amine-based initiator having a nominal functionality of 4 and an aliphatic polyether polyol having a nominal functionality of from 2 to 4. The weight ratio of the polyol derived from the aromatic amine-based initiator and the aliphatic polyether polyol is from about 1:2 to 2:1.

The combination of the polyol component derived from the aromatic amine-based initiator and the aliphatic polyether polyol provide improved compatibility with the aromatic isocyanate component, which results in a polyurethane having improved flexibility and durability. Furthermore, the encapsulated particle, which includes the aforementioned polyurethane, has improved moisture barrier properties, as well as extended and predictable dissolution rates because of the interaction of the polyol component and the aromatic isocyanate component.

DETAILED DESCRIPTION OF THE INVENTION

The encapsulated particle comprises a core particle. The core particle can be utilized in a variety of forms, including in varying sizes and shapes. In certain embodiments, the core particle comprises a fertilizer. As one of ordinary skill in the art will appreciate, a range of fertilizers may be used in conjunction with the inventive encapsulated particle. Typically, the fertilizer includes nitrogen, phosphorous, potash, sulfur, and/or combinations thereof.

In one embodiment, the fertilizer includes nitrogen. Non-limiting examples of suitable fertilizers are urea, ammonium nitrate, urea ammonium nitrate, calcium ammonium nitrate, and combinations thereof. In another embodiment, the fertilizer includes phosphorous. Non-limiting examples of suitable fertilizers that include phosphorous are phosphoric acid, mono-ammonium phosphate, diammonium phosphate, ammonium polyphosphate, ammonium phosphate sulfate, and/or combinations thereof. In yet another embodiment, the fertilizer includes potash. Examples of suitable fertilizers that include potash, or derivatives thereof, are potassium nitrate, potassium chloride, potassium sulfate, and/or combinations thereof. In further embodiments, the fertilizer includes sulfur. Non-limiting examples of suitable fertilizers that include sulfur are ammonium sulfate, sulfur, and/or combinations thereof.

In other embodiments, the core particle comprises a biocide. Examples of biocides include herbicides, insecticides, fungicides, and combinations thereof. It is to be appreciated that alternative forms of core particles can also be used, i.e., core particles that are not fertilizers or biocides, such as flame retardants. Other core particles suitable for the purposes of the present invention, include, but are not limited to, bulbs and seeds, such as grass seeds and flower seeds. In one specific embodiment, the core particle comprises ammonium sulfate.

It is to be appreciated that the encapsulated particle can include any combination of two or more of the aforementioned core particles. In such embodiments, the core particle can comprise, but is not limited to, a blend of core particles, individual sub-particles of the core particle, and/or layers of different core particle compositions. For example, the core particle can comprise an inner-core comprising urea and an outer-core, disposed about the inner-core, and comprising sulfur. Typically, the core particle is anhydrous, or at least anhydrous on its outermost surface (i.e., the core particle is dry) to minimize premature reaction and/or degradation during manufacture and/or storage of the encapsulated particle. Moreover, it is understood that the core particle may consist of, or consist essentially of, any of the aforementioned options.

Although the amount of core particle is not particularly limited, the core particle may be utilized in the encapsulated particle in an amount of from about 75 to 99 wt. %, or, from about 90 to 99 wt. %, or, from about 96 to 98 wt. % based on the weight of the encapsulated particle.

The core particle can have various sizes and shapes. Typically, the core particle is substantially spherical, having a distribution of average diameters of from 0.1 to 5 mm, or, from 1.5 to 2.5 mm, or, from 1.8 to 2 mm. By a distribution of average diameters, we are referring to the size guide number which is defined as the particle size in millimeters of which 50 wt. % of the sample is coarser and 50 wt. % is finer, as determined by a sieve analysis. It is to be appreciated that other sizes and/or shapes of core particles can also be used, such as irregular, oblong or platelet-shaped core particles. In one embodiment, the core particles are larger than described in the above embodiments and be shaped and sized as a conventional tree spike, such that the encapsulated particle be further defined as an encapsulated tree spike (not shown).

The encapsulated particles can be of various sizes and shapes. Typically, the encapsulated particles are substantially spherical, having an average diameter of from about 0.5 to 7.5 mm, of from about 0.5 to 3 mm, or from about 1 to 2 mm. It is also contemplated that the encapsulated particles can be of other shapes, such as irregular, pocked, oblong or platelet shaped encapsulated particles.

The encapsulated particle further comprises a polyurethane disposed about the core particle. For purposes of the present invention, it is to be understood that the terminology "disposed about" encompasses both partial and complete covering and coating of the core particle by the polyurethane. Typically, the core particle is completely or substantially covered by the polyurethane, thereby protecting the core particle from exposure to environmental conditions, such as from premature exposure to moisture. For example, the polyurethane may be disposed about 50, 60, 70, 80, 90, 95, 96, 97, 98, 99, or greater than 99% of the surface area of the core particle. Alternatively still, the polyurethane may be disposed about 100% of the surface area of the core particle.

The polyurethane may be further defined as a polyurethane layer. As one of ordinary skill in the art will appreciate, multiple different layers of polyurethane may be provided about the core particle. These polyurethane layers may be the same or different from one another. The polyurethane may be further defined as a polyurethane layer. As one of ordinary skill in the art will appreciate, multiple different layers of polyurethane may be provided about the core particle. These polyurethane layers may be the same or different from one another. In one embodiment, the encapsulated particle may include a first coating layer. In another embodiment, the encapsulated particle may include the first coating layer and at least one additional coating layer. For example, the encapsulated particle may include 1, 2, 3, 4, 5, 6, or more coating layers disposed about the first coating layer.

Each polyurethane layer typically has an average thickness of from about 5 to 50 microns or, from about 10 to 40 microns, or, from about 15 to 35 microns. It is to be appreciated that the polyurethane layer can be utilized in various thicknesses depending on one or more desired properties, such as the dissolution rate of the encapsulated particle.

In one embodiment, the polyurethane layer is further defined as a first coating layer disposed about the core particle and a second coating layer about the first coating layer. However, other polyurethane layer structures are also contemplated.

In one embodiment, the polyurethane may be utilized in an amount of from about 1 to 10 wt. %, or from about 2 to 8 wt. % of the encapsulated particle. Alternatively, the polyurethane may be utilized in an amount of from about 3 to 7 wt. % of the encapsulated particle. Alternatively still, the polyurethane is utilized in an amount of from about 4 to 5 wt. % of the encapsulated particle. In certain other embodiments, the polyurethane may be utilized in an amount of less than about 1 wt. % of the encapsulated particle.

The amount of the polyurethane layer present in the encapsulated particle is typically determined using the test procedure described immediately below. Initially, 20 g of the encapsulated particle and 500 g of water, e.g. deionized water, are poured into a standard household blender. The blender is activated and the contents of the blender are mixed until the core particle, e.g. urea, is completely dissolved. The contents of the blender are then filtered for solids using pre-weighed filter paper and a Buchner funnel. The filtrand is then dried at approximately 100° C. to substantially remove residual water present with the filtrand. Typically, the filtrand is dried at 100° C. (in an oven) for approximately 30 minutes. After drying, the filtrand is weighed. The amount (% by weight based on the total weight of the encapsulated particle) of the polyurethane layer present in the encapsulated particle is calculated using the amount (in grams) of the filtrand (X) and the amount (in grams) of the encapsulated particle (Y) in the following formula:

Polyurethane Layer(% by weight)=100·($X/Y$)

$X$=the amount of the filtrand (in grams) after drying $Y$=20(initial amount of the encapsulated particle)–$X$.

The polyurethane comprises the reaction product of an aromatic isocyanate component and a polyol component. The aromatic isocyanate component is utilized in an amount from about 20 to 60 wt. % based on the total weight of the aromatic isocyanate component and the polyol component. Alternatively, the aromatic isocyanate component may be utilized in an amount of from about 30 to 50 wt. % based on the total weight of the aromatic isocyanate component and the polyol component. The polyol component may be utilized in an amount of from about 40 to 80 wt. % based on the total weight of the aromatic isocyanate component and the polyol component. Alternatively, the polyol component may be utilized in an amount of from about 30 to 70 wt. % based on the total weight of the aromatic isocyanate component and the polyol component. However, as one of ordinary skill in the art will appreciate, the aromatic isocyanate component and the polyol component may be included in various other amounts.

The aromatic isocyanate component and the polyol component may be provided in an amount such that the ratio of functionality of the aromatic isocyanate component to the OH functionality of the polyol component to the ranges from 1.5 to 1, from about 1.25 to 1, or, from about 1.1 to 1.

The aromatic isocyanate component has a functionality of at least 2 and typically comprises a polyisocyanate having two or more isocyanate functional (NCO) groups. Preferably, the aromatic isocyanate component includes, but is not limited to, monomeric and polymeric methylene diphenyl diisocyanate, monomeric and polymeric toluene diisocyanate, and mixtures thereof. In one specific embodiment, the isocyanate component is commercially available from BASF Corporation of Wyandotte, Mich. under the trade name of Lupranate® M10. Alternatively, the isocyanate component may be commercially available under the trade name of Lupranate® M20, also available from BASF Corporation of Wyandotte, Mich.

Polymeric methylene diphenyl diisocyanates, such as Lupranate® M10, offer high crosslink density and moderate viscosity. Alternatively, monomeric methylene diphenyl diisocyanates such as Lupranate® M Isocyanate offer low viscosity and high NCO content with low nominal functionality. Similarly, toluene diisocyanates such as Lupranate® TDI also offer low viscosity and high NCO content with low nominal functionality. Those skilled in the art will choose a suitable isocyanate component.

The aromatic isocyanate component does not have a particularly limited viscosity and may have a viscosity of from about 1 to 3000 cP, or, from about 20 to 700 cP, or, from about 50 to 300 cP, all at 25° C. The aromatic isocyanate component has a nominal functionality of at least 2, or from 2 to 4, or from 2.2 to 2.7. Preferably, the aromatic isocyanate component has an NCO content of from about 20 to 50 wt. %, or, from about 25 to 40 wt. %, or, from about 30 to 33 wt. % based on the total weight of the isocyanate component.

Referring back, the polyol component comprises a polyol derived from an aromatic amine-based initiator and having a nominal functionality of 4. The polyol component also includes an aliphatic polyether polyol having a nominal functionality of from 2 to 4.

The aromatic amine-based initiator does not have a particularly limited structure but may be of the formula:

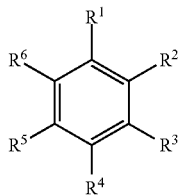

wherein $R^1$ includes one of an alkyl group, an amine group, and a hydrogen atom and each of $R^2$-$R^6$ independently include one of an amine group and a hydrogen atom, so long as at least one of $R^1$-$R^6$ is an amine group. Therefore, it is to be understood that $R^1$ can be any one of an alkyl group, an amine group, or a hydrogen, or any compound including combinations thereof. It is also to be understood that $R^2$-$R^6$ do not have to be identical and each can include an amine group or a hydrogen atom. It is also to be understood that the terminology "an amine group" refers to R—N—H, R—NH$_2$, R—NR'(H), or R—N—R'(R") throughout, where R is an alkyl group, an aryl group, or an alkenyl group.

The aromatic amine-based initiator may include, but is not limited to, a toluene diamine. The toluene diamine preferably includes, but is not limited to, 2,3-toluenediamine; 2,4-toluenediamine; 2,5-toluenediamine; 2,6-toluenediamine; 3,4-toluenediamine; 3,5-toluenediamine; and mixtures thereof.

The polyol derived from the aromatic amine-based initiator may be co-initiated with dipropylene glycol. In one specific embodiment, the polyol derived from the aromatic amine-based initiator is commercially available from BASF Corporation of Wyandotte, Mich. under the trade name of Pluracol® Polyol 1578.

The polyol derived from the aromatic amine-based initiator is typically formed from the aromatic amine-based initiator and a plurality of alkylene oxide units. Examples of suitable alkylene oxide units include ethylene oxide units, propylene oxide units, butylene oxide units, amylene oxide units, alkylene oxide-tetrahydrofuran group mixtures, epihalohydrin mixtures, aralkylene styrene units, and mixtures thereof.

The polyol derived from the aromatic amine-based initiator is not particularly limited but may have a viscosity of from about 4,000 to 30,000 cP, or, from about 10,000 to 25,000 cP, or, from about 16,000 to 21,000 cP at 25° C. The polyol derived from the aromatic amine-based initiator may have a nominal functionality of 4. Although the OH number of the polyol derived from the aromatic amine-based initiator is not particularly limited, it may have an OH number of from about 300 to 600, or, from about 350 to 500, and most preferably, from 380 to 410 mg of KOH equivalent.

The polyol derived from the aromatic amine-based initiator typically has a molecular weight ($M_w$) of from about 180 to 5,000, or, from about 300 to 1,000, or, from about 400 to 700 g/mol. In one specific embodiment, the molecular weight of the polyol derived from the aromatic amine-based initiator is about 550 g/mol.

In one embodiment, the viscosity of the polyol derived from the aromatic amine-based initiator may be from about 10,000 to 15,000 cP at 25° C. to facilitate spraying of the polyol derived from the aromatic amine-based initiator to be sprayed onto the core particle. In another embodiment, the nominal functionality of the polyol is about 4 to facilitate effective reaction of the polyol derived from the aromatic amine-based initiator with the aromatic isocyanate thereby tending to produce a more rigid polyurethane. The OH number of the polyol derived from the aromatic amine-based initiator may be from about 380 to 410 to maximize cross-linking density of the polyurethane.

The polyol derived from the aromatic amine-based initiator tends to be substantially or completely miscible with the aromatic isocyanate component. The miscibility of the aromatic isocyanate component and the polyol derived from the aromatic amine-based initiator may be the result of two primary effects. First, the miscibility is thought to be facilitated by London Forces that create momentarily induced dipoles between similar aromatic moieties of the polyol derived from the aromatic amine-based initiator and the aromatic isocyanate component. The momentarily induced dipoles allow the aromatic isocyanate component and the polyol derived from the aromatic amine-based initiator to mix effectively. Secondly, the miscibility is facilitated by the planar geometry of the aromatic moieties of the polyol derived from the aromatic amine-based initiator and the aromatic isocyanate component that allow for complementary stacking of the polyol derived from the aromatic amine-based initiator and the aromatic isocyanate component. The complementary stacking of the aromatic moieties also allows the aromatic isocyanate component and the polyol derived from the aromatic amine-based initiator to mix effectively.

As described above, the polyol component also comprises an aliphatic polyether polyol. The aliphatic polyether polyol is typically formed from an initiator and a plurality of alkylene oxide units. The initiator may be chosen from glycerin, trimethylol propane, propylene glycol, and combinations thereof. In one specific embodiment, the aliphatic polyether polyol is formed from a propylene glycol initiator. Examples of suitable alkylene oxide units include ethylene oxide units, propylene oxide units, butylene oxide units, amylene oxide units, alkylene oxide-tetrahydrofuran group mixtures, epihalohydrin mixtures, aralkylene styrene units, and mixtures thereof.

In a specific embodiment, the plurality of alkylene oxide units comprises at least 50 wt. % propylene oxide units based on the total weight of the plurality of alkylene oxide units. Alternatively, the plurality of alkylene oxide units comprise at least 50, 60, 70, 80, 90, 95, or 99 wt. % propylene oxide units based on the total weight of the plurality of alkylene oxide units. Alternatively still, the plurality of alkylene oxide units may comprise 100 wt. % propylene oxide units based on the total weight of the plurality of alkylene oxide units. In one specific embodiment, the aliphatic polyether polyol is commercially available from BASF Corporation of Wyandotte, Mich. under the trade name of Pluracol® Polyol P2010.

The aliphatic polyether polyol is not particularly limited but may have a viscosity of from about 100 to 500 cP, or, from about 150 to 350 cP, or, from about 200 to 300 cP, all at 25° C. The aliphatic polyether polyol may have a nominal functionality of from 2 to 4, or, from 2 to 3, or 2. Although the OH number of the polyol derived from the aromatic amine-based initiator is not particularly limited, it may have an OH number, from about 20 to 500, or, from about 25 to 300, or, from about 40 to 70 mg of KOH equivalents.

The aliphatic polyether polyol may have a molecular weight ($M_w$) of from about 200 to 5,000, or, from about 500 to 3,000, or, from about 1,500 to 2,500 g/mol. In one specific embodiment, the molecular weight of the aliphatic polyether polyol is about 2,000 g/mol.

In certain embodiments, the aliphatic polyether polyol interacts with other components in the encapsulated particle in a synergistic fashion. In one embodiment, the nominal functionality of the aliphatic polyether polyol is 2 to facilitate effective reaction of the aliphatic polyether polyol with the aromatic isocyanate component. In another embodiment, the propylene oxide units provide improved moisture barrier properties to the polyurethane.

The ratio of the amount of aliphatic polyether polyol to the amount of the polyol derived from the aromatic amine-based initiators may be chosen based on the compatibility provided by the aromatic isocyanate component and the properties of the resultant polyurethane. In one embodiment, the weight ratio of the polyol derived from the aromatic amine-based initiator and the aliphatic polyether polyol is from about 1:2 to 2:1. Alternatively, weight ratio of the polyol derived from the aromatic amine-based initiator and the aliphatic polyether polyol is from about 1:1.5 to 1.5:1. However, as one of ordinary skill in the art will appreciate, the polyol derived from the aromatic amine-based initiator and the aliphatic polyether polyol may be provided in the polyol component in weight ratios other than those specifically described above.

The polyol component used to form the polyurethane of this invention imparts improved strength and flexibility and improved moisture barrier properties to the polyurethane. The polyol component also contributes to improved reaction and formation times of the polyurethane.

A mixture of the aliphatic polyether polyol and the polyol derived from the aromatic amine-based initiator may have a viscosity of from about 100 to 2,000 cP, or of from about 100 to 400 cP at 53° C. Alternatively, the mixture of the aliphatic polyether polyol and the polyol derived from the aromatic amine-based initiator may have a viscosity of from about 150 to 250 cP at 53° C.

In addition to the polyols described above, the reaction product and/or polyurethane may further comprise one or more additives. The one or more additives are chosen from parting agents, catalysts, fillers, plasticizers, stabilizers, cross-linking agents, chain-extending agents, chain-terminating agents, air releasing agents, wetting agents, surface modifiers, moisture scavengers, desiccants, viscosity reducers, reinforcing agents, colorants, anti-oxidants, compatibility agents, ultraviolet light stabilizers, thixotropic agents, anti-aging agents, lubricants, coupling agents, solvents, rheology promoters, thickeners, anti-static agents, and combinations thereof. The one or more additives may be utilized in the polyurethane in various amounts. It is to be appreciated that the one or more additives may include any combination of the aforementioned options, if employed.

In certain embodiments, the encapsulated particle includes a catalyst component. In one embodiment, the catalyst component comprises tin. Suitable examples of the catalyst component, include, but are not limited to, tin(II) salts of organic carboxylic acids, e.g., tin(II) acetate, tin(II) octoate, tin(II) ethylhexanoate and tin(II) laurate. In one embodiment, the catalyst component is dibutyltin dilaurate, which is a dialkyltin(IV) salt of an organic carboxylic acid. Dibutyltin dilaurates are commercially available from Air Products and Chemicals, Inc. of Allentown, Pa., under the trade name DABCO®. The catalyst component can also comprise other dialkyltin(IV) salts of organic carboxylic acids, such as dibutyltin diacetate, dibutyltin maleate and dioctyltin diacetate. Further examples of the catalyst component may include catalysts comprising zirconium, catalysts comprising titanium, and catalysts comprising copper, as will be appreciated by one of ordinary skill in the art.

Further examples of the catalyst component may include, but are not limited to, iron(II) chloride; zinc chloride; lead octoate; tris(dialkylaminoalkyl)-s-hexahydrotriazines including tris(N,N-dimethylaminopropyl)-s-hexahydrotriazine; tetraalkylammonium hydroxides including tetramethylammonium hydroxide; alkali metal hydroxides including sodium hydroxide and potassium hydroxide; alkali metal alkoxides including sodium methoxide and potassium isopropoxide; and alkali metal salts of long-chain fatty acids having from 10 to 20 carbon atoms and/or lateral OH groups.

Further examples of the catalyst component, include, but are not limited to, specifically trimerization catalysts, for purposes of the present invention, include N,N,N-dimethylaminopropylhexahydrotriazine, potassium, potassium acetate, N,N,N-trimethyl isopropyl amine/formate, and combinations thereof.

Yet further examples of the catalyst component may include tertiary amine catalysts, such as dimethylaminoethanol, dimethylaminoethoxyethanol, triethylamine, N,N,N',N'-tetramethylethylenediamine, N,N-dimethylaminopropylamine, N,N,N',N',N"-pentamethyldipropylenetriamine, tris(dimethylaminopropyl)amine, N,N-dimethylpiperazine, tetramethylimino-bis(propylamine), dimethylbenzylamine, trimethylamine, triethanolamine, N,N-diethyl ethanolamine, N-methylmorpholine, N-ethylmorpholine, bis(2-dimethylamino-ethyl)ether, N,N-dimethylcyclohexylamine (DMCHA), N,N,N',N',N"-pentamethyldiethylenetriamine, 1,2-dimethylimidazole, 3-(dimethylamino)propylimidazole, and combinations thereof. Specific examples of suitable tertiary amine catalysts are commercially available from Air Products and Chemicals, Inc. under the trade name POLYCAT®.

If employed, the catalyst component can be employed in various amounts. In one embodiment, the catalyst component is utilized in the polyurethane in an amount of from about 0.01 to 2 wt. % based on the total weight of the polyol component and the aromatic isocyanate component. More preferably, the catalyst component is utilized in the polyurethane in an amount of from about 0.1 to 1 wt. % based on the total weight of the aromatic isocyanate component and the polyol component. It is to be appreciated that the catalyst component may include any combination of the aforementioned exemplary compounds. In certain embodiments, it should also be appreciated that the encapsulated particle can be formed in the absence of a catalyst component.

In another embodiment, the polyol component or the aromatic isocyanate component comprises an oil. In one or more embodiments, the oil is soluble in the polyol component (including the aliphatic polyether polyol and the polyol derived from the aromatic amine-based initiator). The addition of the oil minimizes agglomeration of the particles during the coating and curing processes. The oil does not substantially chemically react with the aromatic isocyanate component, the polyol component, or other liquids present during the curing of the polyurethane. In other words, the oil is substantially free from substituent groups which are known to react with the polyol component and/or aromatic isocyanate component, such as hydroxyl groups and amine groups. In certain embodiments, less than 10, 5, 1, 0.5, or 0.1 wt. % of a total amount of the oil present reacts with the polyol component, the aromatic isocyanate component, and/or the other liquids present during curing. Alternatively still, in one specific embodiment, none of the oil reacts with the polyol component, the aromatic isocyanate component, and/or the other liquids present during curing.

The oil can be added to the polyol component, the aromatic isocyanate component, or may be added to a mixture of the polyol component and the aromatic isocyanate component. Although not particularly limited, the oil may comprise soybean oil, canola oil, peanut oil, sunflower seed oil, cottonseed oil, methyl esters derived from vegetable oils, and combinations thereof. In one specific embodiment, the oil comprises methyl esters derived from vegetable oils.

If utilized, the oil is typically utilized in the polyurethane in an amount of from about 1 to 30 wt. %, or from about 5 to 25 wt. % based on the total weight of the aromatic isocyanate component and the polyol component. More preferably, the oil is utilized in the polyurethane in an amount of from about 10 to 20 wt. % based on the total weight of the aromatic isocyanate component and the polyol component. However, as will be appreciated by one of ordinary skill in the art, other amounts of the oil may also be used depending on the application of the encapsulated particle.

In another embodiment, the polyurethane layer is formed in the presence of a silicone surfactant. Typically, the silicone surfactant comprises a polyorganosiloxane. A non-limiting example of a suitable polyorganosiloxane is an alkyl pendant organosilicone molecule comprising a polysiloxane backbone and polyether side chains. The alkyl pendant organosilicone molecule of this example can be comb structured or dendrimer structured.

Without being bound or limited by any particular theory, it is believed that the silicone surfactant improves the wetting of the polyol component and the isocyanate component on the core particle. Accordingly, the silicone surfactant may also be described as a wetting agent. It is also believed that the silicone surfactant further improves the adhesion of the polyurethane layer to the core particle. In addition, it is also believed that the silicone surfactant further reduces clumping and agglomeration of the encapsulated particle during and after the encapsulation process. However, it is to be appreciated that the silicone surfactant is not required.

Generally, the yield of encapsulated particles is a measurement of the amount encapsulated particles that pass through a sieve having 4 mm mesh and have a consistent polyurethane layer disposed thereabout. The silicone surfactant decreases agglomeration of the core particles thereby increasing the yield of encapsulated particles. The encapsulation process typically maximizes the amount of encapsulated particles which are individually formed and free flowing and minimizes the amount of encapsulated particles which are agglomerated, therefore resulting in higher overall yields of encapsulated particles.

In one embodiment, the silicone surfactant is a liquid and has a viscosity of from 100 to 1500, alternatively from 200 to 1,000, and alternatively from 650 to 850 centistokes (cSt) at 25° C. The viscosity of the silicone surfactant may vary outside of the ranges above, but is typically both whole and fractional values within those ranges.

Specific examples of suitable silicone surfactants include, but are not limited to, TEGOSTAB® BF 2370, commercially available from Goldschmidt AG of Essen, Del., DABCO® DC5043 commercially available from Air Products and Chemicals, Inc. of Allentown, Pa., and NIAX® Silicone L-5340 and L-620, both commercially available from Momentive Performance Materials of Albany, N.Y. A particularly suitable silicone surfactant is NIAX® Silicone L-620, a polyalkyleneoxidemethylsiloxane copolymer. The silicone surfactant may be present in the polyurethane layer in an amount of from 0.01 to 10, alternatively from 0.05 to 5, and alternatively from 0.1 to 3, parts by weight based on 100 parts by weight of the polyurethane layer. The parts by weight silicone surfactant may vary outside of the ranges above, but is typically both whole and fractional values within those ranges.

The encapsulated particle may optionally include a sealant disposed about the polyurethane in one or more embodiments. The sealant may be provided in the form of a layer (i.e., a "sealant layer") on the polyurethane. The sealant may seal imperfections in the polyurethane layer, may improve the flow characteristics of the encapsulated particles, and may provide improve moisture barrier properties. The sealant may comprise organic waxes, such as paraffinic wax, vegetable wax, triglycerides, microcrystalline thermoplastic polymers, mineral oils, petroleum waxes or combinations thereof. More particularly, the sealant may comprise paraffinic oil, paraffinic wax, vegetable wax, triglyceride, microcrystalline wax, petrolatum, olefin, polyethylene, and combinations thereof. The sealant is further described in U.S. Pat. Nos. 5,538,531; 5,698,002; 5,984,994; 5,466,274; 5,478,375; 5,300,135; and 5,423,897; the contents of each are hereby incorporated by reference. Furthermore, as will be appreciated by one of ordinary skill in the art, the sealant may comprise other materials other than those described above. The sealant may include various additives, as will be appreciated by one of ordinary skill in the art. For example, the sealant may include various polymers to improve the abrasion resistance and barrier properties, anti-blocking adjuvants to improve the handling characteristics, dyes, and other known adjuvants.

Generally, the sealant has a melting point below the melting point of the core particle and the polyurethane. In one or more embodiments, the sealant may have a melting point below 80° C. and flow at the temperature of the application process. The sealant may be non-tacky after application to the polyurethane at temperatures below 60, 50, or 40° C. Furthermore, the sealant may have a melt viscosity less than about 1500 cP or less than about 1000 cP at the application temperature to allow for good flowability on the core particle.

The encapsulated particle may include the sealant in various amounts depending on the desired release rate of the encapsulated particle. In one embodiment, the encapsulated particle may comprise an amount of sealant layer of from about 0.1 to 10 wt. %, or, of from about 0.1 to 5 wt. % based on the total weight of the encapsulated particle. Alternatively, the encapsulated particle may comprise an amount of sealant of from about 0.2 to 1.5 wt. % based on the total weight of the encapsulated particle.

Formation of the Encapsulated Particle

A method of forming the encapsulated particle is described below. To form the encapsulated particle, the core particle is provided. The isocyanate component and the polyol component are then applied to the core particle. Upon contact (and while under reaction conditions understood in the polyurethane art), the isocyanate component and the polyol component begin to react to form the polyurethane disposed about the core particle to form the encapsulated particle.

In one embodiment, the polyol component is applied to the core particle prior to applying the aromatic isocyanate component to the core particle. In another embodiment, the aromatic isocyanate component is applied to the core particle prior to applying the polyol component to the core particle. Accordingly, it is contemplated that the aromatic isocyanate component and the polyol component are applied sequentially. Alternatively still, the aromatic isocyanate component and the polyol component may be applied simultaneously or substantially simultaneously, either from mixed sources of the polyol component and the aromatic isocyanate component or from separate sources of the polyol component and the aromatic isocyanate component.

Furthermore, the method may include forming a first coating layer and at least one additional coating layer. These polyurethane layers may be the same or different from one another and may be formed through repeated applications of the aromatic isocyanate component and the polyol component.

In one embodiment, the polyol derived from the aromatic amine-based initiator and the aliphatic polyether polyol are pre-blended to form a mixture. The mixture can optionally include the oil described above. The mixture is typically then applied to the core particle as a single unitary component. Alternatively, the polyol derived from the aromatic amine-based initiator and the aliphatic polyether polyol can be applied to the core particle separately.

The components can be applied by various methods known in the art. Examples of suitable methods of encapsulation, include, but are not limited to, bulk coating, tumbling and roller drums, sheet coating, pan coating, fluidized-bed coating, co-extrusion, spraying and spinning disk encapsulation. Additional encapsulation methods suitable for use are well known to those of ordinary skill in the polyurethane and chemical engineering art. In certain embodiments, the components are sprayed, atomized, and/or fogged onto the core particles, while the core particles are being agitated in suitable equipment. Typically, spraying, atomizing, and/or fogging the components onto the core particle results in a substantially uniform, complete, and defect-free polyurethane disposed about the core particle. Spraying, atomizing, and/or fogging the components also tend to result in a thinner and less expensive polyurethane disposed about the core particle. However, several application steps can be used to build-up the thickness of the polyurethane, if so desired. For example, a first coating layer of the polyurethane (i.e., the aromatic isocyanate component and the polyol components) can be applied to the core particle and allowed to cure before application of a second coating layer. It will also be appreciated that any number of layers of the polyurethane can be applied to the core particle, depending on the needs of the application.

Spraying, atomizing and fogging of the components can occur via use of nozzles, such as one nozzle for each component supplied thereto, or nozzles that have two or more components premixed and supplied thereto. Generally, at least one nozzle can be used to apply the aromatic isocyanate component, and at least one nozzle can be used to apply the polyol component, to the core particle. As described and exemplified above, various orders of application can be employed to form the polyurethane.

To maximize coverage, the polyol and aromatic isocyanate components are typically applied to the core particles by spraying droplets or atomizing or fogging the components onto the core particles as the core particles are tumbled in a rotary blender or similar apparatus. As another example, the core particles can be coated with the components in a rotary drum blender equipped with at least one, typically at least two spinning disk atomizers. Tumblers, drums, or rollers including baffles can also be used, as understood in the art. Alternatively, the core particles can be provided directly to a carrier, e.g., a screened conveyor belt and the components can be applied to the core particles on the conveyor belt, e.g., by spraying or sheeting, to form the encapsulated particles. Further, at least one of the components, e.g., the polyol component, may be present on the core particles prior to application of the remaining components of the reaction product, e.g., the aromatic isocyanate component. Prior to the polyurethane fully curing, the encapsulated particles are typically kept moving or agitated to avoid agglomeration.

The amount of the components to be applied and mixed with the core particles tends to be dependent upon several variables including the specific components employed, the size and type of core particle used, the intended use of the encapsulated particle, desired thickness of the polyurethane, and the desired properties of the encapsulated particle.

It is to be appreciated that various types of the encapsulated particles can be supplied to consumers in blends, such as encapsulated particles having different core particles, e.g., different types of fertilizers, such as nitrogen and potash, nitrogen and sulfur, etc. The encapsulated particles can also have different physical properties, such as different sizes and shapes, different dissolution rates, different hardness, etc. Such properties are described below. Generally, the encapsulated particles do not agglomerate or minimally agglomerate, such that the encapsulated particles are pourable for ease of use. In one embodiment, the core particles are free flowing, and thereby do not clog apparatuses (e.g., a fertilizer spreader) used to supplying and/or spreading of the encapsulated particles.

The encapsulated particles can have various hardness characteristics (or "crush" strength) depending on several variables including, the specific components and amounts thereof employed, size and shape of the core particle, size and shape of the encapsulated particle, and thickness of the polyurethane. Hardness of the encapsulated particles provides for longer life of the encapsulated particles, such that the encapsulated particles have excellent handling and storage/shelf life. Specifically, the polyurethane of the present invention tends to provide for increased resiliency of the encapsulated particle.

The encapsulated particle of the present invention is also useful for providing the core particle, e.g., fertilizer, in a time-released manner. Time release, i.e., time required for the polyurethane to be perforated such that the core particle can be released to the surrounding environment, typically depends on several variables including, but not limited to, the specific components and amounts thereof employed, size and shape of the core particle, size and shape of the encapsulated particle, and thickness and composition of the polyurethane.

Time release of the encapsulated particle is also associated with dissolution rate of the encapsulated particle. As understood in the art, dissolution rate is a measurement of how much of the core particle is dispersed into the surrounding environment per unit time. For example, dissolution rate may refer to the amount of fertilizer released to the surrounding soil over time once the encapsulated particle is exposed to moisture, e.g., from rain or irrigation.

The dissolution rate is determined by weighting 90 g of distilled water into a 4 oz. plastic bottle. For each test, 10 g of the respective encapsulated particles are added to the plastic water bottle and the contents are dispersed through gentle swirling. The contents of the plastic water bottle are allowed to rest until the next measurement interval. Before the next measurement is taken, the contents of the plastic water bottle are gently swirled to distribute the encapsulated particles uniformly. Immediately after swirling, the refractive index of the water solution is determined using a Milton Roy model 33.46.10 refractometer. The refractive index for each type of encapsulated particles is plotted against standard curves of concentration of ammonium sulfate. From these curves, the dissolution rate is calculated (percentage of the ammonium sulfate dissolved in the water).

In one embodiment the encapsulated particle comprises less than about 6 wt. % of the polyurethane and where about 5 to 50 wt. % of the core particle dissolves within 24 hours. In one embodiment, the encapsulated particle comprises less than about 6 wt. % of the polyurethane and where about 10 to 30 wt. % of the core particle dissolves within 24 hours. In another embodiment, the encapsulated particle comprises less than about 6 wt. % of the polyurethane and where about 15 to 25 wt. % of the core particle dissolves within 24 hours. However, as one having ordinary skill in the art will appreciate, other dissolution rates are contemplated depending on the needs of the particular application. The dissolution rate can also be determined after the encapsulated particle 10 is abraded to test the durability of the coating formed thereon.

Generally, the encapsulated particles of the present invention have a uniform dissolution rate, i.e., a near steady-state release of the core particle over a period of time. Alternatively, or in addition to, the encapsulated particles of the present invention may have a time-delayed release, e.g., the core particle will begin to dissolve and therefore release some period of time after the encapsulated particles are first exposed to a sufficient amount of moisture to penetrate the polyurethane.

The following examples, illustrating the encapsulated particles of the present invention, are intended to illustrate and not to limit the present invention.

EXAMPLES

Three polyurethanes are prepared by mixing their respective components together in beakers. The reactants used to form each of the three polyurethanes are provided below in TABLE 1. Composition A includes the aromatic isocyanate component, the polyol derived from the aromatic amine-based initiator, and the aliphatic polyether polyol, in accordance with one embodiment of the inventive composition. Composition B is a comparative example that includes the aromatic isocyanate component and the polyol derived from the aromatic amine-based initiator, but lacks the aliphatic polyether polyol. Composition C is a comparative example that includes the aromatic isocyanate component and the aliphatic polyether polyol, but lacks the polyol derived from the aromatic amine-based polyether polyol.

TABLE 1

Polyurethanes

| Composition A (Inventive Composition) | Composition B (Comparative Composition) | Composition C (Comparative Composition) |
| --- | --- | --- |
| 3.65 g Isocyanate A | 5 g Isocyanate A | 1.26 g Isocyanate A |
| 3.18 g Polyol A | 5 g Polyol A | — |
| 3.18 g Polyol B | — | 8.74 g Polyol B |
| 0.04 g Catalyst A | — | 0.08 g Catalyst A |

Isocyanate A is commercially available from BASF Corporation of Florham Park, NJ under the tradename of Lupranate ® M10.
Polyol A is commercially available from BASF Corporation of Florham Park, NJ under the tradename of Pluracol ® 1578.
Polyol B is commercially available from BASF Corporation of Florham Park, NJ under the tradename of Pluracol ® 2010.
Catalyst A is commercially available from Air Products of Allentown, PA under the tradename of Polycat ® 9.

Films of polyurethanes A, B, and C are prepared by spreading each polyurethane on an aluminum foil sheet, placing another aluminum foil sheet on top of the polyurethane, pressing the top aluminum foil sheet to form a layer of polyurethane having a uniform thickness of about 0.5 mm, and curing the polyurethane in an oven at 55° C. to form a film. Compositions A and B formed uniform polyurethane films, whereas the components of Composition C separated under these conditions and did not cure, and thus, did not form a polyurethane. As will be appreciated by one of ordinary skill in the art, Composition A shows superior cure properties over Composition C.

To measure the flexibility of the films formed above, the top aluminum foil sheet is separated from the film, and each film is suspended on a horizontal surface with a 1.2 cm gap. Using a Universal Testing Machine (Tinius Olsen Model H5KS) with a blade attachment, the force necessary to force the film through the gap is measured. The blade attachment has a thickness of 0.09 cm. The Universal Testing Machine is set to descend at a speed of 4 cm per minute.

As shown below in Table 2, the force necessary to force the film through the gap is much lower for the film formed from inventive Composition A than the film formed from comparative Composition B because the film formed from Composition B is much less flexible than the film formed from Composition A. Accordingly, encapsulated particles which utilize the polyurethane formed from Composition A have superior durability and resiliency during handling when compared to the encapsulated particles formed from Composition B or C.

TABLE 2

Flexibility Testing Results of Polyurethane Films

| Polyurethane Formed From Composition A | Polyurethane Formed From Composition B |
| --- | --- |
| 5.8N | 32.9N |

The polyurethanes formed from Compositions A, B, and C are also used to form encapsulated particles. The polyurethane layer of these examples includes a first coating layer and a second coating layer.

Each of the polyurethanes is applied to ammonium sulfate granules using the following procedure: 200 g of ammonium sulfate granules are heated to 55° C. in a stainless steel pan contained in a thermostatic water bath. The ammonium sulfate granules have an average diameter of 1.9 mm. After heating, a first coating layer of 4 g is formed by adding the polyol component, optionally with the catalyst, to the ammonium sulfate granules and mixing by hand to spread the polyol component onto the surface of the ammonium sulfate granules. Immediately after the ammonium sulfate granules are coated with the polyol component, the aromatic isocyanate component is added while continuing to mix. The polyol component reacts with the isocyanate component to form the first coating layer. The first coating layer is allowed to cure before the application of the second coating layer. The second coating layer is formed in the same manner as the first coating layer. The application of both the first and second coating layers results in a polyurethane layer having a total weight about 4 wt. % based on the total weight of the encapsulated particle. The polyurethane layer has a total thickness of about 22 microns.

Each coating layer formed from Composition A cures in about 6 minutes. Each coating layer formed from Composition B cures in about 4 minutes. Each coating layer formed from Composition C requires a cure temperature of about 94° C. in order for an adequate cure. Furthermore, even after heating, each coating layer formed from Composition C cures in about 30 minutes. Thus, Encapsulated Particles A includes polyurethane formed from Composition A, Encapsulated Particles B includes polyurethane formed from Composition B, and Encapsulated Particles C includes polyurethane formed from Composition C.

The dissolution rates of Encapsulated Particles A, B, and C are shown below in Table 3.

TABLE 3

Percentage of Ammonium Sulfate Released in 1 Day for Encapsulated Particles

| | 24 Hour Dissolution Rate (Wt. % Percentage of Ammonium Sulfate Released in 24 Hours) |
|---|---|
| Encapsulated Particle A | 20 |
| Encapsulated Particle B | 59 |
| Encapsulated Particle C | 94 |

Table 4 below provides a comparison of the dissolution rates of encapsulated particles with and without the sealant layer. For all of the compositions in Table 4, 4 wt. % of a polyurethane is applied to the ammonium sulfate core particle. The polyurethane included 31.7 wt. % of the aliphatic polyether polyol, 31.7 wt. % of the polyol derived from the aromatic amine-based initiator, and 36.7 wt. % of the aromatic isocyanate component. Sealant 1 included 50 wt. % of paraffin wax and 50 wt. % of an antiblocking adjuvant. Sealant 2 included 75 wt. % paraffin wax and 25 wt. % of an adjuvant to improve barrier properties. Sealant 3 included 100 wt. % of petrolatum.

TABLE 4

Percentage of Ammonium Sulfate Released for Encapsulated Particles with a Sealant Layer

| Sealant Layer | 1 Hour Dissolution Rate (Wt. % Percentage of Ammonium Sulfate Released in 1 hour) | 24 Hour Dissolution Rate (Wt. % Percentage of Ammonium Sulfate Released in 24 hours) | 7 Day Dissolution Rate (Wt. % Percentage of Ammonium Sulfate Released in 7 days) |
|---|---|---|---|
| Sealant Layer 1 at 0.5 wt. % | 1.2 | 2.4 | 16.8 |
| Sealant Layer 2 at 0.5 wt. % | 0.6 | 3.0 | 22.4 |
| Sealant Layer 3 at 0.5 wt. % | 1.8 | 4.7 | 20.5 |
| No Sealant 1 | 5.3 | 12.5 | 52.1 |
| No Sealant 2 | 4.1 | 11.9 | 52.1 |
| No Sealant 3 | 4.1 | 10.7 | 52.1 |

From the results, it is clear that Sealant Layers 1-3 result in a lower percentage of ammonium sulfate released within the first 7 days, as the encapsulated particles which did not include the sealant layers released more than double as much ammonium sulfate as the encapsulated particles which included a sealant layer.

It is to be understood that the appended claims are not limited to express and particular compounds, compositions, or methods described in the detailed description, which may vary between particular embodiments that fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and/or in combination and provides adequate support for specific embodiments within the scope of the appended claims.

It is also to be understood that any ranges and subranges relied upon in describing various embodiments of the present invention independently and collectively fall within the scope of the appended claims and are understood to describe and contemplate all ranges, including whole and/or fractional values therein, even if such values are not expressly written herein. One of skill in the art readily recognizes that the enumerated ranges and subranges sufficiently describe and enable various embodiments of the present invention and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims and may be relied upon individually and/or collectively and provide adequate support for specific embodiments within the scope of the appended claims.

In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention has been described in an illustrative manner and it is to be understood that the terminology which has been used is intended to be in the nature of words of description rather than of limitation. Many modifications and variations of the present invention are possible in light of the above teachings and the invention may be practiced otherwise than as specifically described.

What is claimed is:

1. An encapsulated particle comprising:
   a core particle; and
   a polyurethane disposed about said core particle and comprising the reaction product of an aromatic isocyanate component having a nominal functionality of at least 2 and a polyol component;
   wherein said aromatic isocyanate component is utilized in an amount of from about 20 to 60 wt. % based on the total weight of said aromatic isocyanate component and said polyol component, and
   wherein said polyol component is utilized in an amount of from about 40 to 80 wt. % based on the total weight of said aromatic isocyanate component and said polyol component, and
   wherein said polyol component comprises;
   a polyol derived from an aromatic amine-based initiator and having a nominal functionality of 4, and
   an aliphatic polyether polyol having a nominal functionality of from 2 to 4,
   wherein the weight ratio of said polyol derived from said aromatic amine-based initiator and said aliphatic polyether polyol is from about 1:2 to 2:1.

2. An encapsulated particle of claim 1 wherein said polyol component comprises said polyol derived from the aromatic amine-based initiator and said aliphatic polyether polyol in a weight ratio of from about 1:1.5 to about 1.5 to 1.

3. An encapsulated particle of claim 1 comprising less than about 6 wt. % of said polyurethane based on the total weight of said encapsulated particle,
wherein from about 5 to 50 wt. % of said core particle dissolves in water at 25° C. within 24 hours.

4. An encapsulated particle of claim 1 comprising less than about 6 wt. % of said polyurethane based on the total weight of said encapsulated particle,
wherein from about 10 to 30 wt. % of said core particle dissolves in water at 25° C. within 24 hours.

5. An encapsulated particle of claim 1 wherein said core particle comprises a fertilizer comprising urea, potash, phosphate, or ammonium sulfate.

6. An encapsulated particle of claim 1 wherein said core particle comprises ammonium sulfate.

7. An encapsulated particle of claim 1 wherein said aromatic amine-based initiator comprises the formula:

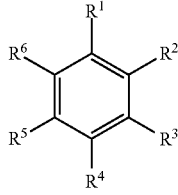

wherein $R^1$ is an alkyl group, an amine group, or a hydrogen atom,
wherein $R^2$, $R^3$, $R^4$, $R^5$, and $R^6$ are each independently an amine group or a hydrogen atom, and
wherein at least one of said $R^1$-$R^6$ is said amine group.

8. An encapsulated particle of claim 1 wherein said aliphatic polyether polyol is formed from an initiator chosen from glycerin, trimethylol propane, propylene glycol, and combinations thereof.

9. An encapsulated particle of claim 1 wherein said aliphatic polyether polyol is formed from a propylene glycol initiator and a plurality of alkylene oxide units, and
wherein said plurality of alkylene oxide units comprises at least 50 wt. % propylene oxide units based on the total weight of said plurality of alkylene oxide units.

10. An encapsulated particle of claim 1 wherein said polyol component further comprises from about 5 to 25 wt. % of an oil that is soluble in said polyol component based on the total weight of said aromatic isocyanate component and said polyol component.

11. An encapsulated particle of claim 10 wherein said oil is chosen from soybean oil, canola oil, peanut oil, sunflower seed oil, cottonseed oil, methyl esters derived from vegetable oils, and combinations thereof.

12. An encapsulated particle of claim 1 further comprising a sealant disposed about said polyurethane, wherein said sealant is chosen from an organic wax, a thermoplastic polymer, a mineral oil and combinations thereof.

13. An encapsulated particle of claim 1 further comprising a sealant disposed about said polyurethane, wherein said sealant is chosen from a paraffinic oil, a paraffinic wax, a vegetable wax, a triglyceride, a microcrystalline wax, petrolatum, an olefin, polyethylene, and combinations thereof.

14. An encapsulated particle comprising:
a core particle comprising a fertilizer;
at least one polyurethane disposed about said core particle and comprising the reaction product of an aromatic isocyanate component having a nominal functionality of at least 2 and a polyol component;
a sealant disposed about said polyurethane, wherein said sealant is chosen from an organic wax, a thermoplastic polymer, and combinations thereof; and
an oil that is soluble in said polyol component and that is utilized in an amount of from about 5 to 25 wt. % based on the total weight of said aromatic isocyanate component and said polyol component,
wherein said aromatic isocyanate component is utilized in an amount of from about 20 to 60 wt. % based on the total weight of said aromatic isocyanate component and said polyol component;
wherein said polyol component is utilized in an amount of from about 40 to 80 wt. % based on the total weight of said aromatic isocyanate component and said polyol component,
wherein said polyol component comprises;
an polyol derived from an aromatic amine-based initiator and having a nominal functionality of 4, and
an aliphatic polyether polyol having a nominal functionality of from 2 to 4,
wherein the weight ratio of said polyol derived from said aromatic amine-based initiator and said aliphatic polyether polyol is from about 1:2 to 2:1.

15. A method of forming an encapsulated particle, said method comprising:
providing a core particle;
providing an aromatic isocyanate component having a nominal functionality of at least 2;
providing a polyol component comprising;
a polyol derived from an aromatic amine-based initiator and having a nominal functionality of 4, and
an aliphatic polyether polyol having a nominal functionality of from 2 to 4;
applying the aromatic isocyanate component to the core particle; and
applying the polyol component to the core particle,
wherein the polyol component and the aromatic isocyanate component react to form polyurethane disposed about the core particle;
wherein the polyol component is utilized in an amount of from about 40 to 80 wt. % based on the total weight of the aromatic isocyanate component and the polyol component;
wherein the aromatic isocyanate component is utilized in an amount of from about 20 to 60 wt. % based on the total weight of the aromatic isocyanate component and the polyol component; and
wherein the weight ratio of the polyol derived from the aromatic amine-based initiator and the aliphatic polyether polyol is from about 1:2 to 2:1.

16. The method of claim 15 further comprising forming a first coating layer about the core particle and forming at least one additional coating layer about the first coating layer.

17. The method of claim 15 further comprising applying a sealant to the polyurethane,
wherein the sealant is chosen from a paraffinic oil, a paraffinic wax, a vegetable wax, a triglyceride, a microcrystalline wax, petrolatum, an olefin, polyethylene, and combinations thereof.

18. The method of claim 15 wherein the polyol component further comprises an oil that is soluble in the polyol component.

19. The method of claim 15 wherein the polyol component has a viscosity of from about 100 to 300 cP at 53° C.

20. The method of claim 15 wherein the aliphatic polyether polyol is formed from a propylene glycol initiator and a plurality of alkylene oxide units, and
   wherein the plurality of alkylene oxide units comprises at least 50 wt. % propylene oxide units based on the total weight of the plurality of alkylene oxide units.

* * * * *